US008296962B2

(12) United States Patent
Ferrara et al.

(10) Patent No.: US 8,296,962 B2
(45) Date of Patent: Oct. 30, 2012

(54) SYSTEM AND AUTO-ALIGNMENT METHOD FOR DETERMINING POSITION USING A DISCRETE CONTACT PROBE

(75) Inventors: Keith S. Ferrara, Stratford, CT (US); Mario Carozza, Danbury, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 319 days.

(21) Appl. No.: 12/730,797

(22) Filed: Mar. 24, 2010

(65) Prior Publication Data

US 2010/0250010 A1   Sep. 30, 2010

Related U.S. Application Data

(60) Provisional application No. 61/162,841, filed on Mar. 24, 2009.

(51) Int. Cl.
*G01B 7/00* (2006.01)
*G01D 21/00* (2006.01)
(52) U.S. Cl. ............... 33/542; 33/520; 33/644
(58) Field of Classification Search ............ 33/543, 33/520, 644, 542
See application file for complete search history.

(56) References Cited

U.S. PATENT DOCUMENTS

| | | | | |
|---|---|---|---|---|
| 2,466,380 A | * | 4/1949 | Clark | 33/642 |
| 3,241,243 A | * | 3/1966 | Speer | 33/503 |
| 4,080,741 A | * | 3/1978 | Siddall et al. | 33/502 |
| 4,128,943 A | * | 12/1978 | Muhlethaler | 33/542 |
| 4,380,873 A | | 4/1983 | Ayres et al. | |
| 5,179,788 A | * | 1/1993 | Jadach | 33/644 |
| 5,259,119 A | * | 11/1993 | Yoshioka et al. | 33/502 |
| 5,339,031 A | * | 8/1994 | Chern | 324/219 |
| 5,737,244 A | * | 4/1998 | Ruck | 702/153 |
| 6,314,656 B1 | * | 11/2001 | Morel et al. | 33/644 |
| 6,467,178 B1 | * | 10/2002 | Svensson et al. | 33/286 |
| 6,760,679 B1 | | 7/2004 | Carney et al. | |
| 6,802,133 B2 | * | 10/2004 | Jordil et al. | 33/504 |
| 2003/0226272 A1 | * | 12/2003 | Finefield | 33/542 |
| 2004/0177670 A1 | | 9/2004 | Gilson et al. | |

FOREIGN PATENT DOCUMENTS

| | | |
|---|---|---|
| EP | 0269795 | 6/1988 |
| GB | 2089251 | 6/1982 |

* cited by examiner

*Primary Examiner* — Christopher Fulton
(74) *Attorney, Agent, or Firm* — Cesari and McKenna, LLP (57) ABSTRACT

A method and system of aligning a probe to wells includes holding the probe at one potential and holding the wells at a different potential, moving the probe to an estimated center position above a selected well, lowering the probe into the selected target well, moving the probe in positive and negative directions along first and second axial dimensions until changes in potential are detected at the probe to indicate electrical contact between the probe and the selected well, and calculating a center location of the selected well along the first and second axial dimensions as mid-points between the points of contact for the respective axial dimensions. The method and system further include lowering the probe into contact with a floor of the selected well and calculating a center location along a third axial dimension as a predetermined distance above the position of the probe. The method and system determine center locations for other wells based on known spacing between wells and the calculated center locations of one or more selected wells.

21 Claims, 6 Drawing Sheets

SYSTEM AND AUTO-ALIGNMENT METHOD FOR DETERMINING POSITION USING A DISCRETE CONTACT PROBE

CROSS-REFERENCE TO RELATED APPLICATIONS

The present application claims the benefit of U.S. Provisional Patent Application Ser. No. 61/162,841, which was filed on Mar. 24, 2009, by Keith S. Ferrara et al. for a SYSTEM AND AUTO-ALIGNMENT METHOD FOR DETERMINING XYZ POSITION USING DISCRETE CONTACT PROBE and is hereby incorporated by reference.

BACKGROUND OF THE INVENTION

1. Field of the Invention

The invention relates generally to alignment systems and, more particularly, to alignment systems that utilize electrical contact for precise alignment.

2. Background Information

Systems such as differential scanning calorimeters, or DSCs, for analyzing properties of materials, including phase changes during heating or cooling, and so forth, are complex, finely tuned instruments. The systems require precise movement of samples of the materials for analysis into and out of sample and control furnaces that are each small numbers of millimeters in diameter. The furnaces are sized to heat and cool rapidly, and thus, an analysis of a number of samples can be done relatively quickly by transporting the samples into and out of the respective furnaces. Typically, automated transport systems are used to move the samples.

The samples are held in pans, and each furnace is contoured to include a well that holds the sample pan during the analysis. Each pan, which is sized to fit within the furnace well, is thus an even smaller number of millimeters in diameter. The pans are, in turn, held in sample wells of a sample tray. The sample wells may, for example, be arranged in a grid such that the individual samples can be identified by their locations within the grid. The automated transport system moves a designated sample, i.e., a sample specified by its grid location, into the well of a designated furnace for analysis and thereafter returns the sample to the appropriate sample well. The transport system of interest includes a probe that regulates a vacuum to both pick up the sample pans from and deposit the sample pans in the sample and furnace wells. The transport system must operate with precision, to avoid damage to the sample pans, the furnaces and the probe through unintended contact.

The analytic results may also be adversely affected if the sample pan is imprecisely placed within a furnace well. If, for example, the sample pan is placed off-center and, in particular, if the pan touches the wall of the furnace, the heating or cooling may be affected. Indeed, certain samples may spill if the pans tip through contact with the furnace walls as the pans are lowered into the furnace wells, and thus adversely affect the analysis or even the operation of the furnace. Further, the pans may dent if they come in contact with the walls of the furnaces during transport, and the dented pans may alter the results of the analysis by, for example, creating relative hot or cold spots during heating.

The damage to the pans and/or furnaces may thus compromise the analysis of certain or all of the samples, requiring the repeating of the analysis with newly prepared samples. Further, the system may have to be idled for repair to the furnaces, the probe and/or other components of the transport system.

At start up and/or periodically the transport system must be aligned with the sample wells and the wells in the furnaces. To align the probe with the center of, for example, the well in one of the furnaces, known prior systems may require a skilled technician to manually direct the probe to the appropriate center position "by eye." Alternatively, the systems may instead require the use of one or more strategically placed optical sensors to align the probe with the center position, based on, for example, reflections from the furnace well. Further, similar alignment is required with the sample tray wells, and so forth. The overall alignment is complex and may require a service engineer to periodically re-align system components to compensate for changes in the system mechanics as a result of the maneuvering of the probe by the technician and/or changes in the operations of the transport system components, such as the sensors, over time.

SUMMARY OF THE INVENTION

An autosampler system that includes automatic alignment sub-system aligns and calibrates the movement of a probe, which is movable in three angular and/or linear dimensions, with a target well by determining x, y and z axial dimensions of the target well based on controlled contact between the probe and the target well. The system maintains the probe at a low DC potential and the target well at ground potential. For x,y,z alignment with the center of a target well, the probe is moved in a controlled manner along the z axis and into electrical contact with the bottom, or floor, of the well, with the contact being indicated by a change in potential at the probe. The probe position at the point of contact is retained, and the probe is then moved above the floor a predetermined distance, for example, one-half the predetermined depth of the well, to determine the position of the center along the z axial dimension. From this position the probe is moved in a controlled manner along, for example, the x axis in a positive direction and into electrical contact with a wall of the target well, with the contact again being indicated by a change in potential at the probe. The system then uses the probe position at the point of contact as one end of the x axial dimension. The system moves the probe in a negative direction along the same axis until the probe again comes into contact with the target wall, to determine a second end of the x axial dimension. The system determines the center of the x axial dimension as mid-way between the end points. The system similarly determines the end points and center of the y axial dimension and calculates the center location of the target as the coincidence of the centers of the x, y and z axial dimensions. The system then calibrates the movement of the probe based on the known geometry of the target well.

The system may determine the locations of the centers of associated wells that are in a predetermined arrangement or spacing relative to the target well, based on the alignment and calibration of the probe movement and the predetermined arrangement or spacing of the associated wells relative to the target well.

BRIEF DESCRIPTION OF THE DRAWINGS

The invention description below refers to the accompanying drawings, of which.

DETAILED DESCRIPTION OF AN ILLUSTRATIVE EMBODIMENT

Referring now to FIGS. 1-4, an autosampler system 110 that includes an automatic alignment sub-system is attached to and operates with a differential scanning calorimetry (DSC) system 100. The autosampler system includes a probe 106 that transports a sample from a designated sample well 208 of a sample tray 108 to one of the furnaces 220, and deposits the sample in the furnace, or more precisely within a well 222 that is within the furnace.

Figure 1:
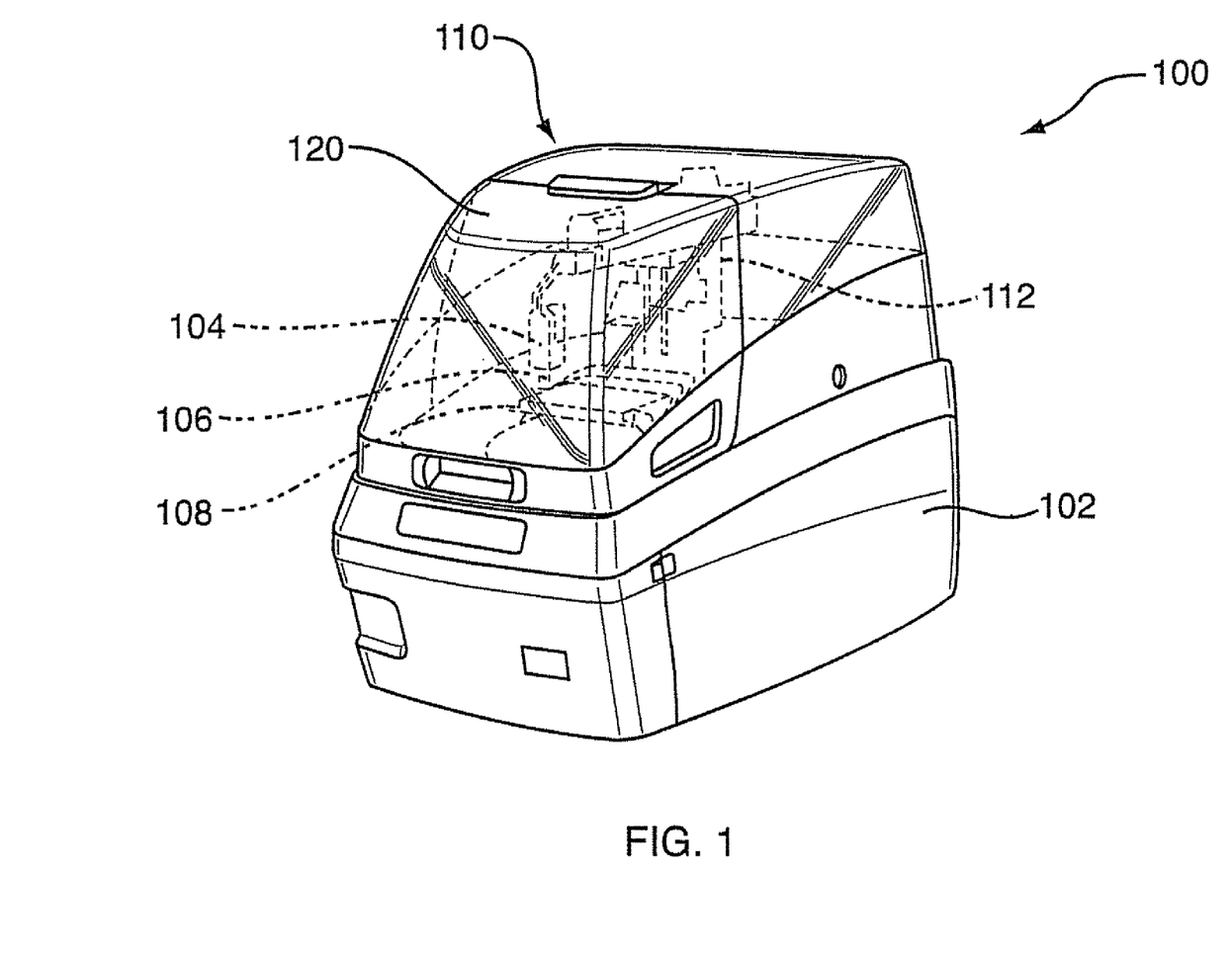
FIG. 1 is an illustration of a DSC with an automatic alignment system constructed in accordance with the invention.
Figure 2:
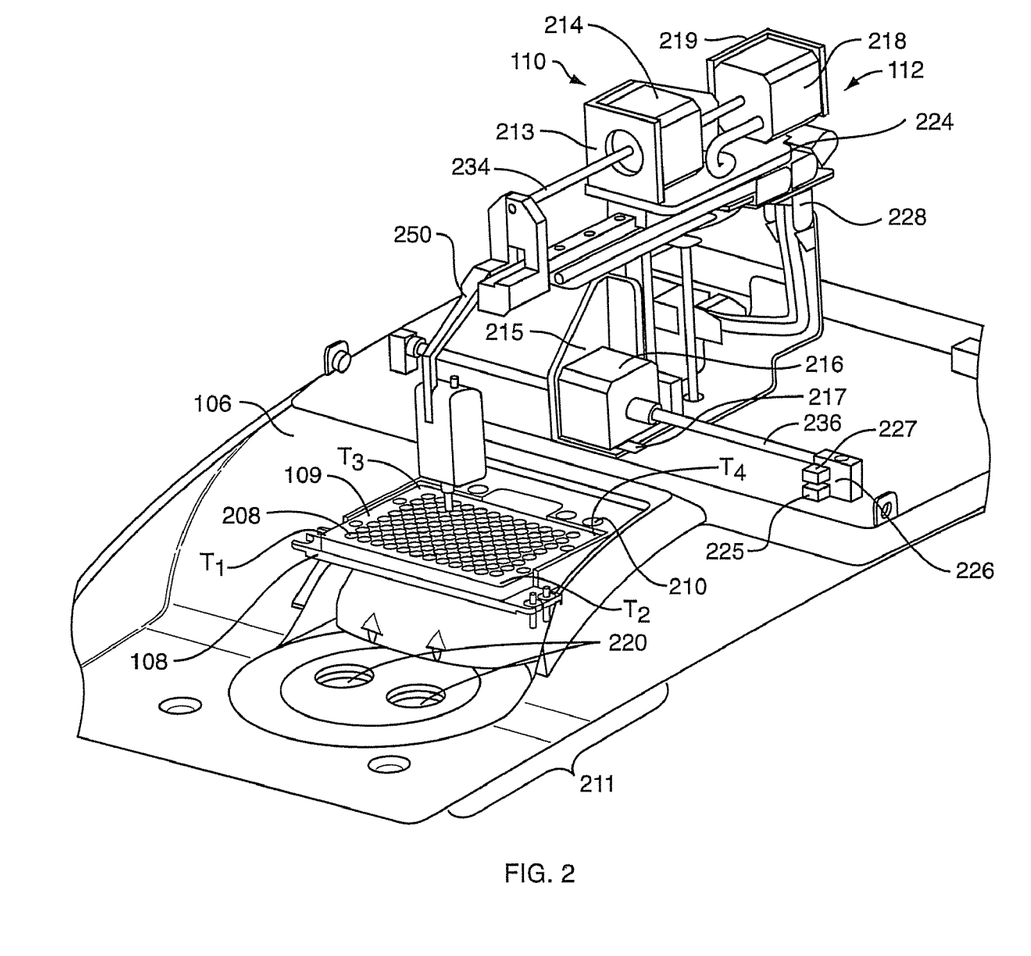
FIG. 2 is a more detailed view of the system of FIG. 1.
Figure 3:
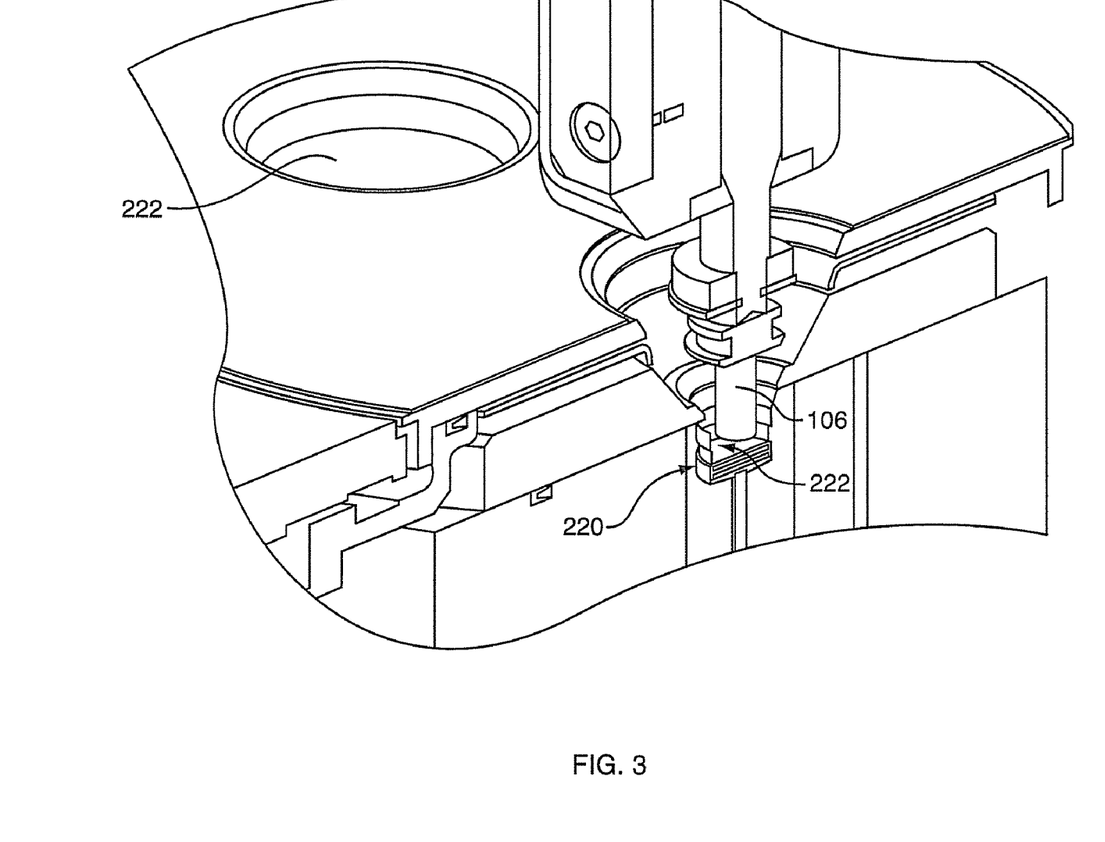
FIG. 3 is a more detailed cross sectional view of the system of FIG. 2.

The DSC system 100 heats the sample in the furnace well 222 and performs an analysis, to determine a precise temperature and energy of a transition of interest in the sample. The autosampler system 110 then returns the sample from the furnace well 222 to the appropriate sample well 208 after the analysis is completed. The autosampler system similarly transports the remaining samples, which are included in an array 209, in the example, a grid, of sample wells, to and from the wells of the respective furnaces for analysis. The DSC system thus includes heaters and other components (not shown) that are housed in a body 102 and operate in a known manner to heat the samples in the furnaces and determine when and at what temperature and energy the transitions of interest occur in the respective samples. As shown, the DSC system includes a latched cover 120 that opens and closes such that the sample tray 108 can be inserted into or removed from the system at appropriate times.

The furnaces 220 typically have diameters of small numbers of millimeters, and are contoured to include smaller diameter wells 222, in this example, approximately 8 millimeters, into which the sample pans are deposited. The samples for analysis are held in the sample wells 208 in pans (not shown) that are sufficiently small to fit into the wells 222 of the furnaces 220. In the example, the pans have diameters ranging approximately from 6.7 to 7.8 millimeters, and the sample wells of the sample tray are sized to hold the pans. The pans are transported from the sample wells to the furnace wells by the probe 106, which is approximately 3 millimeters in diameter and utilizes a vacuum to lift and carry the pans. The probe thus has a vacuum outlet (not shown). The autosampler system 110 essentially turns off the vacuum at the probe once the pan is transported to and placed within the furnace well, and the probe is withdrawn before the furnace is operated to heat the sample. In the example, the system 110 operates a valve (not shown) that controls the vacuum at the probe. The system generates the vacuum in a known manner using, in the example, a pump (not shown).

The probe 106 is similarly utilized to place a lid (not shown) on the furnace well 222 after the sample pan is in place in the furnace well 222. The probe thus transports the lid from a lid well 210 in the sample tray 108 to the furnace and deposits the lid to enclose the sample pan within the furnace. Once the lid is in place on the furnace, the system 110 moves the probe to a designated remote or "home" position while the analysis is performed. Thereafter, the system returns the probe to the furnace to transport the lid and then the pan to their respective wells 210, 208 in the sample tray 108.

The movement of the probe 106 is precisely controlled by a plurality of stepper motors 214, 216, 218, as discussed in more detail below. In the example, the stepper motors are connected to antibacklash screws (not shown) that are mounted on linear slides 234, 236 (z-axis slide is hidden from view in the drawing) over which the motors move. The motors are attached to movable chassis 213, 215 and 219 that are, in turn, attached to an arm 250 that moves in accordance with the movement of the chassis to provide the linear motion to the probe. The antibacklash screws are included to ensure that reversing the direction of the motor does not result in an error in alignment. Other known motor designs that provide precise, calibrated linear or angular motion may also be used, such as, for example, DC motors with encoders.

As discussed above, it is critical that the autosampler system 110 move the designated samples between the furnace wells 222 and the sample wells, all of which are small numbers of millimeters in diameter, without damaging the sample pans, the furnaces well 222 or the probe 106. As also discussed, the system must place lids that are similarly small numbers of millimeters in diameter on the furnaces. To ensure the precise movement of the particular sample pans and lids, the autosampler system determines the dimensions of certain target wells, i.e., selected sample, lid and/or furnace wells 208, 210, 222, and calibrates the movements of the probe relative to the target wells. In addition, the system calculates the x, y, z coordinates of the centers of the target wells, to align the probe with the centers. The system also uses the alignment and calibration information along with the geometry of, for example, the sample well array 209, to determine the center locations of other wells that are in predetermined positions relative to the selected, or target, wells for which the locations of the centers were calculated.

Figure 4:
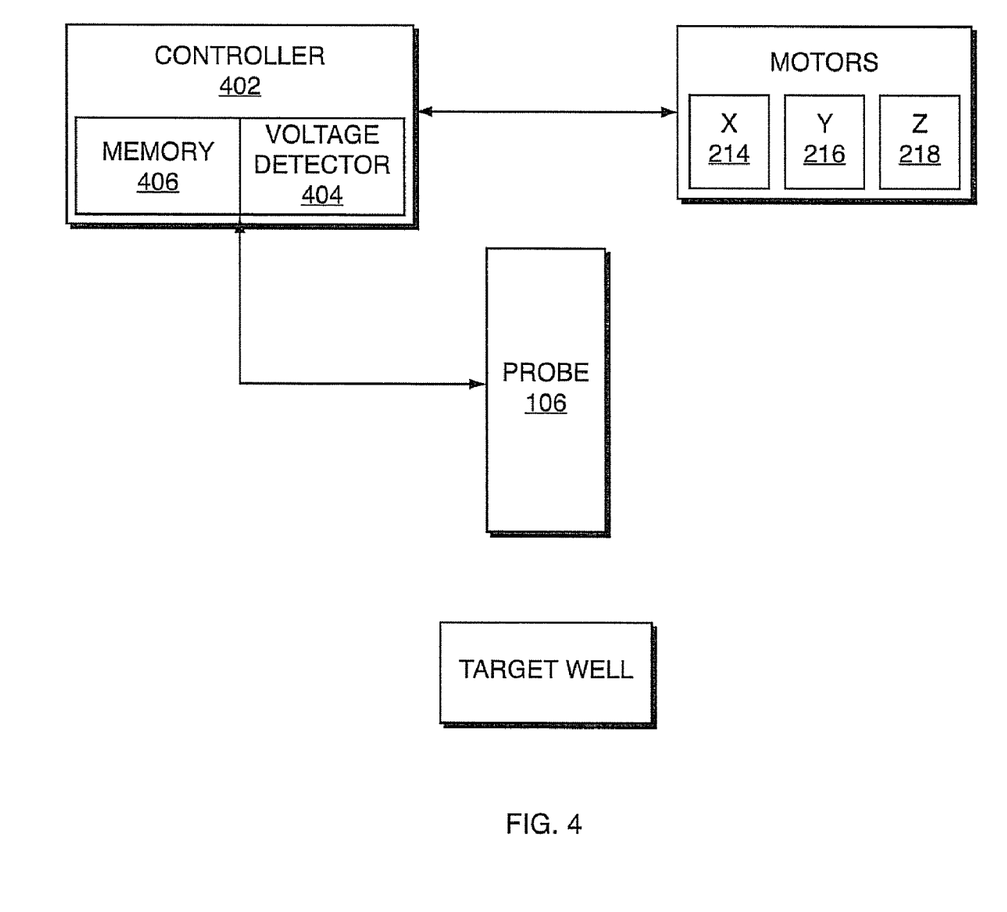
FIG. 4 is a functional block diagram of the automatic alignment system of FIG. 1.

Before aligning the probe 106 with the centers of the lid, sample and furnace wells 210, 208 and 222, the system determines a designated home position for the probe. The system retains in a memory 406, or otherwise has available from another source such as, for example, a database, predetermined lengths of travel along each of the three axes of movement, namely, the x, y and z axes, for a given target area of interest. In the example, the target area of interest is the sample tray and furnace area 211 of the DCS 100. The predetermined lengths, which in the example are in steps and/or portions thereof, represent the distances from axial maximum positions to the home position. The maximum positions are determined using limit sensors 224, 226, 228 that are positioned near, or alternatively at, the ends of the respective slides over which the motors move. The home position is the position from which the distances to the respective furnace wells, sample wells and lid wells are determined.

To determine the home position, the autosampler system 110 first moves the probe 106 to a nominal position relative to the target area 211. The nominal position may be, for example, a previously calculated position or a stored predetermined position. The movement of the probe is calibrated first along the z axis. This avoids damage to the probe, sample wells 208, lid wells 210 and/or furnace wells 222 should the probe be in a position that is sufficiently low to result in unintended contact were the probe instead to move first along the x or y axes. For ease of explanation, we refer to movement along the x, y and z axes as movement in positive and negative directions, which are stated as, for example, +X and −X directions. The directions are toward or away from designated ends of the respective slides and in the example the designated ends are the ends on which the limit sensors 224, 226 and 228 are located.

The autosampler system 110 moves the probe 106 from the nominal position by stepping the stepper motor 218 along the z axis in the +Z direction, which is up from the target area, until the limit sensor 228 associated with the z axis trips. The limit sensor is an optical sensor that consists of a sensor element 225 and a light source 227. Accordingly, the stepper motor 218, operating under the control of a controller 402, steps the probe in the +Z direction along the z axis until a flag 219, which is attached to the chassis 215, moves between the light source 227 and the sensor element 225 and thus blocks the light from reaching the sensor element.

The system then moves the probe in the −Z direction in "micro-steps," that is, in movements that are calibrated in relatively small numbers of degrees of rotation of the associated screw, until the chassis 215 has just moved the motor 218 out of the sensor's range of detection and thus the flag 219 no longer blocks light from reaching the sensor element. The system then sets the motor position as the maximum position or end of travel along the z axis, and determines a "zero" position along the z axis by subtracting the predetermined length of travel over the z-axis from the maximum position.

The autosampler system 110 repeats the same process for the x and y axes starting with the probe 106 at the zero position of the z axis. The system thus moves or steps the probe, for example, in the +X direction under the control of the x-axis stepper motor 214 up to the point of detection by the associated optical sensor 224. The system then steps the motor in micro-steps in the −X direction just past the detection range of the sensor, to determine a maximum point on the x axis, and subtracts the predetermined x-axis length of travel from the maximum point to determine the zero point on the x axis. The system next starts the probe at the zero positions of the x and z axes and moves the probe in the +Y direction under the control of the y-axis stepper motor 216 up to the point of detection of the associated optical sensor 226. The system then moves the probe in the −Y direction by stepping the motor in micro-steps to just past the detection range of the sensor, to determine a maximum point on the y axis, and calculates the zero point on the y axis by subtracting the predetermined y-axis length of travel from the maximum point. The system sets the home position as the coincidence of the zero positions along the respective x, y and z axes.

Alternatively, the system may continue to move the probe a predetermined number of steps or micro-steps in the positive directions past the tripping of the sensors before moving the probe in the negative directions in micro-steps along the axes to determine the maximum positions.

The autosampler system 110 next precisely aligns the movement of the probe 106 with the furnace wells 222, the sample wells 208 and lid wells 210, in order to control the pick up and transfer of the samples and lids between the respective sample and lid wells and the furnaces and furnace wells. The system automatically determines the dimensions and center locations of the furnace, lid and sample wells through controlled contact between the probe and the floor and walls of one or more selected, or target, furnace wells, lid wells and/or sample wells, and the extrapolation of the measurements to associated furnace, lid and/or sample wells based on the overall geometry of the target area 211. In the example, the system determines the dimensions and center locations of all of the furnace and lid wells, and particular sample wells, namely, the sample wells at the corners $T_1$-$T_4$ of the grid 209. The wells for which the dimensions are determined through contact with the probe are sometimes referred to herein collectively as "target wells."

The probe 106 is made of an electrically conductive material, and the auto sampler system 110 provides a small DC charge, in the example, 5 volts, to the probe 106. The autosampler system also holds the furnace wells 222 and the sample tray 108, and thus, the lid wells 210 and the sample wells 208 at ground potential. Physical contact between the probe and any of the furnace, lid and sample well floors and walls results in electrical contact of the probe to ground and produces a detectable change in potential at the probe. The autosampler system thus determines the dimensions of the target wells and calculates the center location coordinates based on controlled contact between the probe and the floors and walls of the respective target wells.

In the example, the system determines the dimensions and center locations of the lid wells 210 first and then the sample wells 208 and finally the furnace wells 222. The system further determines the z axis dimension, or height, of the top surface 109 of the sample tray 108 and uses this information to determine a minimum distance to lower the probe 106 into the sample and lid wells during alignment. This allows the system to perform the alignment even when sample pans and lids are contained in the wells, since the pans and lids will sit lower in the wells. Accordingly, the alignment can take place after a fully prepared sample tray is loaded into the system.

Alternatively, the system could perform the calibration and alignment to the wells in any order. Further, the system could determine the relative heights of the floors of the lid and sample wells in the same manner as is discussed below with reference to the alignment and calibration to the furnace wells.

For alignment, and with reference also to FIGS. 5 and 6A-H, the autosampler system controller 402 directs the stepper motors 214 and 216 to move the probe 106 from the calculated home position along x and y axes to a position above a flat section of the top surface 109 of the sample tray 108 that is adjacent to a selected lid well 210. The controller then directs the z-axis stepper motor 218 to lower the probe, that is, move the probe in the −Z direction, in micro-steps until the probe comes into electrical contact with the top surface of the sample tray, which is at ground potential. The contact is indicated by a drop in potential at the probe and is detected by a voltage detector 404 that operates under the control of the controller. The system next sets a minimum distance that the probe must move in the −Z direction from the zero z axis position to ensure that the probe will contact the vertical wall of the selected lid well during the alignment operation. and stores the position in the memory 406. The system then raises the probe 106 in the +Z direction a predetermined number of steps or micro-steps above the surface of the sample tray, that is, out of contact with the sample tray, and moves the probe to an estimated x,y center position above the selected lid well. (step 502), FIG. 6A. The system may, for example, raise the probe to the home z-axis position to move the probe to the estimated position. The system then lowers the probe in the −Z direction by the set distance to place the probe within the well (step 504).

Figure 6A:
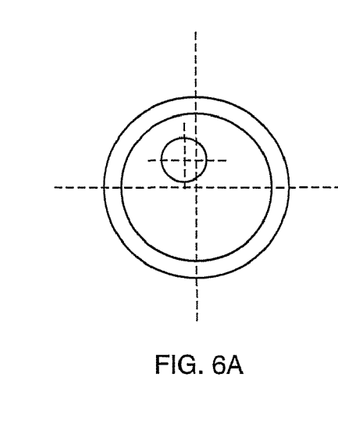
FIGS. 6A-6H are illustrations of the steps of the alignment operation of FIG. 5.
Figure 6B:
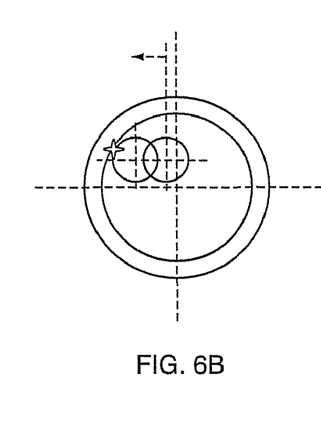
Figure 6C:
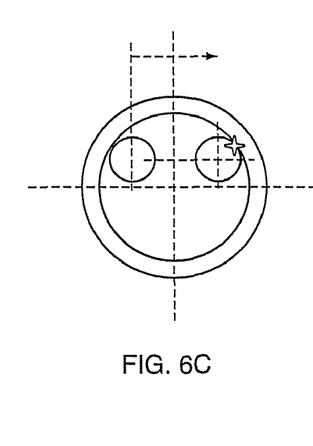
Figure 6D:
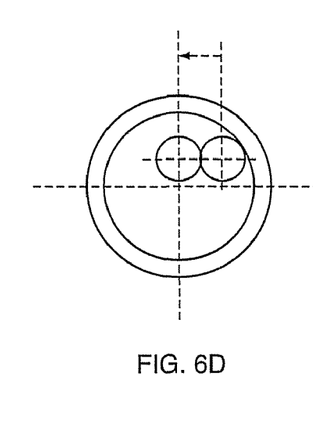

Next, the system moves the probe 106 slowly along the x axis in one direction, for example, in micro-steps in the +X direction, until a drop in the potential at the probe is detected by the voltage detector 404 (step 506), FIG. 6B. The system retains the probe location, i.e., the corresponding location of the x axis stepper motor 216, as one end of the x axial dimension of the target well. The system 110 moves the probe 106 slowly, in the example, in micro-steps, in the negative direction along the x axis, until a second voltage drop is detected (step 508), FIG. 6C. The second voltage drop indicates that the probe has again come into electrical contact with the wall of the target well, and the system uses the location of the probe, i.e., the corresponding location of the x-axis stepper motor, as a second end of the x axial dimension of the well. The system then determines the center point of the x axis as midway between the two end locations (Step 514), FIG. 6D. In the example, the autosampler system 110 counts the number of steps and/or micro-steps utilized to move the probe from the first end to the second end of the axial dimension and then divides the count by two, to calculate the axial center in numbers of steps and/or micro-steps.

Figure 6E:
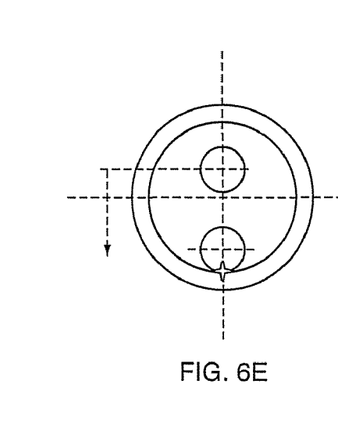
Figure 6F:
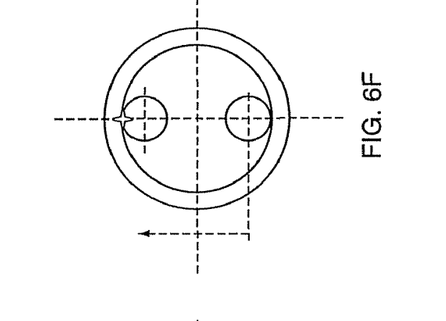

The system next moves the probe to the center position of the x axis, and starts the process of determining the center of the y axial dimension of the well (step 510). The system utilizes the y-axis stepper motor 214 to step the probe 106 slowly along the y axis in a given direction, for example, in micro-steps in the +Y direction, until a voltage drop at the probe is detected by the voltage detector 404 to indicate that the probe has made electrical contact with the well wall. (step 512), FIG. 6E. The system uses the location of the probe, i.e., the location of the motor, as one end of the y axial dimension of the well. The stepper motor then moves the probe slowly, i.e., in micro-steps, in the −Y direction until a second voltage drop is detected (step 514), FIG. 6F.

Figure 6G:
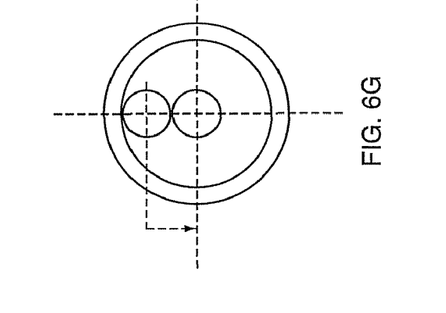
Figure 6H:
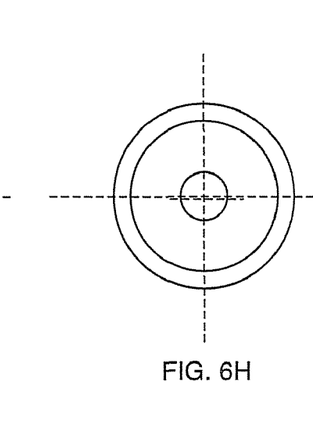

The system uses the probe location at the second voltage drop as a second end of the y axial dimension of the well. The system then determines the center point of the y axis as half-way between the two end locations, and the system moves the probe to the center position (step 516), FIG. 6G. The system may thus count the number of steps and/or micro-steps required to move the probe from the first end to the second end of the y axial dimension, and divide the number of steps by two, to determine the center point of the y axial dimension of the well. The x,y center of the well is then the calculated centers of the x and y axes, as indicated by FIG. 6H.

Figure 5:
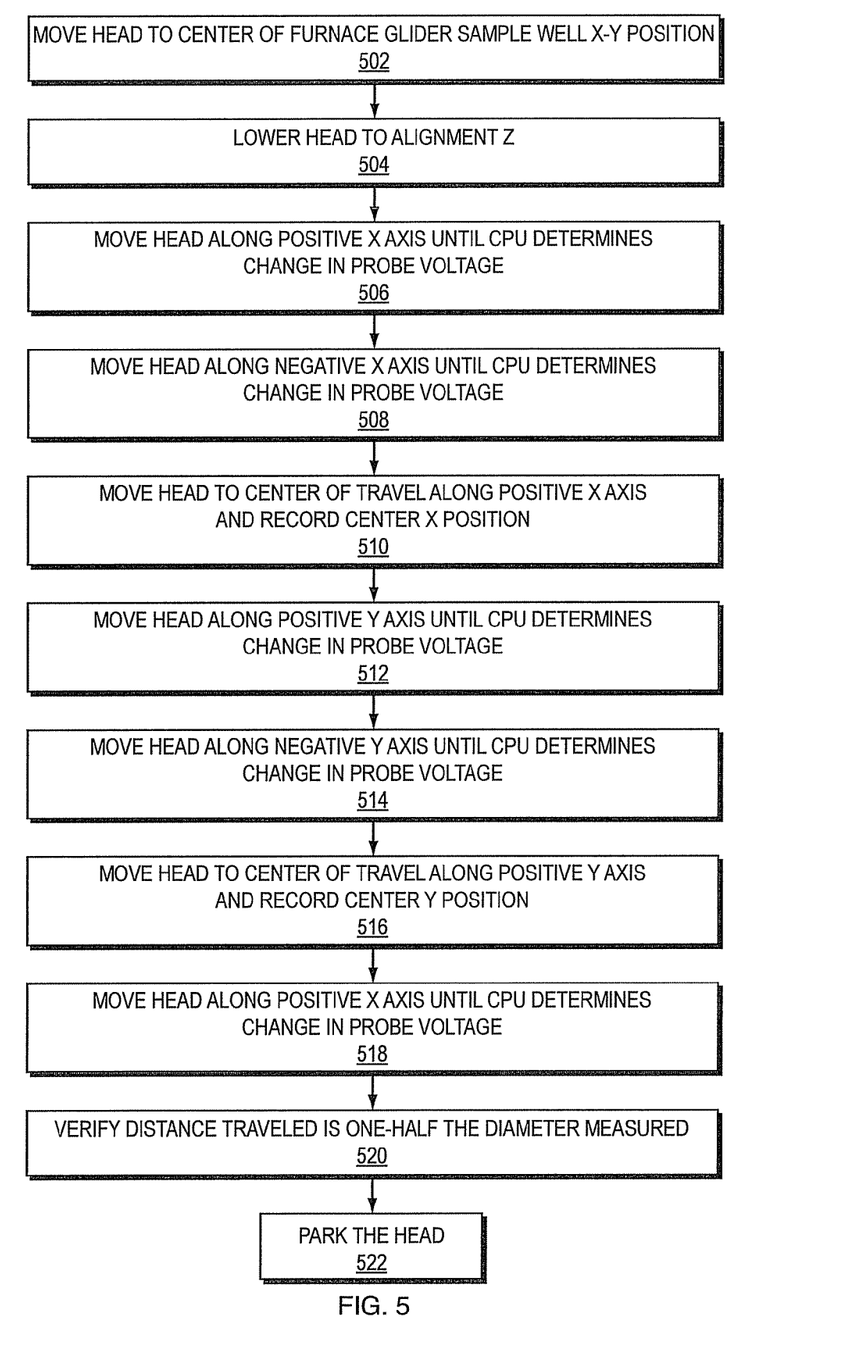
FIG. 5 is a flow chart of an alignment operation.

The autosampler system 110 may next verify that the indicated x, y location is the center of the lid well 210 by stepping the probe 106 in micro-steps from the calculated center position in one direction along one of the axes, in the example, the probe is stepped along the x axis in the positive direction until a voltage drop is detected to indicate contact with the well wall (step 518). Alternatively, the probe may be moved along the y axis. When the voltage drop is detected, the system determines if the probe traveled one-half of the earlier calculated distance, i.e., one-half the number of micro-steps, of the x axial dimension. If so, the system verifies that the calculated x, y, z location is the center of the furnace (step 520). The system may then "park" the probe in the home position, to end the alignment process for the particular well (step 522). If the calculated location is not the center, however, the system 110 may adjust the position of the probe along the z axis, that is, up or down as appropriate, and repeat the process. Otherwise, the system notifies a user that there may be problem with the furnace, such as, for example, damage to the furnace well.

The system repeats the same process with respect to the remaining lid wells 210. Thus, the system moves the probe 106 from the home position to a flat surface adjacent to a given lid well and sets the associated z axis distance that the probe will be lowered into the well during alignment and then moves the probe to an estimated center position of the given well and determines the dimensions and centers along the x and y axes, and verifies that the indicated x, y locations are the centers of the respective lid wells, all based on the electrical contact of the probe with the wall of the well to signify the ends of the respective axial dimensions. Alternatively, the system may move the probe from the calculated center of the first lid well 210 directly to an estimated x,y center position above the second lid well, to start the alignment process at the second well. To do this, the system first raises the probe to the home or zero position along the z axis and then utilizes known or stored information about the spacings between the two lid wells to determine the position to which to move the probe.

The system further determines the distance of the center of each lid well from the zero or home position of the probe based on the movement of the probe from the home position during alignment, such that the system can then calibrate the movement of the probe with the known underlying geometry of the target area 211.

The system 110 next determines the dimensions and locations of the centers of the respective sample wells 208. To do this the system determines the dimensions and calculates the center locations of a number of selected sample wells, and uses the calculated information to determine the coordinates of the center locations of the remaining wells based on the known relative spacing of the wells in the grid 209. The selected sample wells, in the example, are located at the four corners $T_1$-$T_4$ of the grid. The system then determines skews along the rows and columns of the grid based on the differences in the x and y coordinates of the center locations for the sample wells in the same rows and columns, and applies the skews, to determine the precise locations of the centers of the respective sample wells in the grid. In this way, the system compensates for changes in the placement, that is, misalignment, of the sample tray 108.

The system uses stored sample tray information and the calibration information from the lid well alignment to move the probe 106 from the calculated home position to a flat surface area adjacent to a first selected sample well 208. In the example, the system moves the probe proximate to the sample well on a first corner $T_1$ of the grid 209. The system then determines the Z axis, or height, position of the top of the sample tray by lowering the probe until a voltage drop is detected by the voltage detector 406. The system retains the height information and uses the information to the minimum distance the probe should be lowered in the −Z direction into the selected sample wells during alignment to ensure that the probe will contact the walls or vertical surfaces of the wells and avoid contact sample pans that may be contained in the wells.

The system next raises the probe 106 a predetermined number of steps from the surface of the tray 108 and moves the probe by a predetermined x and/or y distance, to position the probe over the selected corner sample well 208. The system then moves the probe in the −Z direction by the set distance to bring the probe into the well. Next, the system slowly steps the probe, e.g., in micro-steps, along a first axis in one direction, in the example, along the x axis in the positive direction, until the probe comes into electrical contact with the wall of the sample well. The system notes this location as one end of the x axial dimension and determines the second end by stepping the probe across the well in the −X direction until the probe again contacts the wall of the well. The system next calculates the center of the x axis as one-half the number of steps and/or micro-steps required to move the probe across the well. The system then starts the probe at the center of the x axis and repeats the process along the y axis, to determine the x,y center of the well. As discussed, the system may then verify the center location.

The system next moves the probe to each of the remaining corner sample wells, i.e., at the corners $T_2$ through $T_4$, and determines the dimensions and the locations of the centers of the respective wells in the same manner. The system then translates the center coordinates to distances from the home or zero positions of the x and y axes in the manner discussed above with reference to the lid wells 210.

The system determines skew in the x and y directions over the grid 209 based on the differences in the x and y coordinates of the centers of the selected sample wells 208 along rows and columns of the grid, respectively. For example, the system determines the skew in the x axis based on the differences in the number of steps and/or micro-steps that define the x-axis coordinates, or distances, of the center locations of sample wells at the corners $T_1$ and $T_2$ and/or $T_3$ and $T_4$. The system determines the skew in the y axis based on the differences in the y coordinates, or distances, of the center locations of the sample wells at the corners $T_1$ and $T_3$ and/or $T_2$ and $T_4$.

Other sample wells, that is, wells in other locations in the grid, may be utilized in addition to or instead of the corner wells to determine the x and y skew.

To move the probe, for example, to the center of a sample well of interest that is proximate to one of the corner wells, the system uses the calculated center location of the corner well, the predetermined spacing information for the sample wells, and the calculated x and y skews to calculate the center location of the sample well of interest.

The autosampler system 110 performs a similar operation to determine the x,y,z centers of the furnace wells 222. The system utilizes the calibration information to move the probe to an estimated center position above a given furnace well. Before determining the dimensions of the furnace well, however, the system lowers the probe, that is, moves the probe in the −Z direction, by a predetermined number of steps or micro-steps into the well looking for any obstructions, which may be, for example, a sample pan and/or lid left therein. As described below, the system determines an obstruction by an increase in the back-pressure of the vacuum that occur at probe positions that differ from the expected positions.

The system looks first for a lid and a second time for a sample pan by lowering the probe 106 into the furnace well 222 by corresponding predetermined distances in the −Z direction. If a lid and/or a sample pan is found the probe transports them to a waste receptacle (not shown) next to the sample well tray 108. The system then determines the position of the floor of the furnace well by moving the probe in the −Z direction until the voltage detector 406 detects a voltage drop at the probe. The system then moves the probe a predetermined distance, which is one-half the known depth of the furnace well, from the floor in the +Z direction to a center of the well along the z axis. The system also determines the contact positions along the respective x and y axes, and so forth, to determine the x and y axial dimensions of the furnace well, and calculates the center positions along the x and y axes as discussed above. The system has thus determined the locations of the lid, sample and furnace wells as distances from the probe home position, and the system can then direct the probe to move the samples pans and lids between designated wells without risk of damage to the samples, wells and/or the probe. The controlled movement of the probe during alignment, through micro-steps of the stepper motors, prevents the probe from damaging or being damaged by the respective wells. As discussed, the probe need only be in electrical contact with the target wells, which means that only slight physical contact is required.

Using the calculated center locations, the autosampler system 100 can also detect obstacles and determine that particular samples are missing during the transport operations. If, for example, the probe picks something up in fewer steps along a given axis than expected, the system 110 signals the presence of an obstacle and, as discussed, transports the obstacle to the waste receptacle. The autosampler system 110 may similarly signal a missing sample pan or lid if the probe does not pick up something after the probe is moved to the calculated center location of the associated well 208, 210, 222.

The system determines whether the probe has picked up a sample pan or a lid by monitoring the back-pressure at the vacuum outlet. An increase in back-pressure, for example, indicates the probe has picked up something. If the back-pressure at the vacuum outlet does not increase at what should be the center location of a given furnace, lid or sample well, the system may, as appropriate, move the probe in any or all of the x, y and z directions within the dimensions of the well in an attempt to pick up the appropriate lid or sample pan, before signaling that the lid or sample pan is missing. If the back-pressure at the vacuum outlet is less than expected after a pick up, it may indicate that, for example, a lid is dented, and thus, not flat against the end of the vacuum outlet. Accordingly, the system may signal to the operator that the selected lid requires replacement. The vacuum back-pressure is similarly monitored to determine if a sample or lid has been dropped, and the system signals the operator accordingly.

The system has been described by way of a particular example. However, the autosampler system that includes the automatic alignment system may be used with other instrumentation requiring precise positioning of samples in target wells through automatic or robotic movement. The sample, lid and/or furnace wells may be other shapes than round, such as, for example, elliptical, or may be of any concave shape, with the probe contacting different boundaries to determine dimensions in two or three linear and/or angular axial directions, and the arrangement of the sample wells may be other that a grid, for example, a circle, an ellipse and so forth. Further, the limit sensors may be other than optical interruption sensors and may be, for example, conventional photo detectors or other types of motion sensors, the stepper motors may instead be any conventional motors for linear and/or angular movement that can be calibrated, as mentioned, the motors may be DC motors with encoders. Further, the probe may be grounded and the target wells held to a DC potential slightly above ground, or alternatively, the probe and the target wells may be held at different relative potentials without being grounded. In addition, if the autosampler system is newly connected to the DSC the probe may be maneuvered by hand to place the probe in estimated positions with respect to the furnaces for the first alignment operation, to avoid problems associated with the mechanical tolerances of the system components. Once the system calibrates to the DSC, however, the system can then automatically align the probe with the remaining wells in the target area.

What is claimed is:

1. An automated alignment system consisting of:
   one or more target wells held at a first potential;
   a probe having a tip held at a second potential;
   one or more motors for moving the probe relative to the target wells; and
   a controller configured to:
   detect changes in potential at the probe,
   direct the motors to move the probe to an estimated position in which the probe tip extends within a given target well and move the probe along first and second axes to determine dimensions of the given target well by determining first and second end points of the first and second axes as the locations at which the potential at the probe tip changes along the first and second axes,
   direct the motor to move the probe along a third axis into electrical contact with a floor of the given target well based on a change in potential at the probe tip, and
   calculate a center location of the given target well as the coincidence of mid-points of the first, second, and third axes that are calculated based on the endpoints of the first and second axes, and a mid-point of the third axis calculated based on a location of the floor of the given target well and a known depth of the given target well.

2. The system of claim 1 wherein the controller is further configured to:
   direct the motors to move the probe along the first axis until a first change in potential of the probe tip is detected, the controller using the position of the probe as a first end point of the first axis,
   direct the motors to move the probe in a reverse direction over the first axis until a second change in potential is detected, the controller using the position of the probe as a second end point of the first axis, the controller calculating the center of the first axis as the mid-point between the first end point and the second end point of the first axis,
   direct the motors to move the probe to the calculated center of the first axis and move the probe along the second axis until a first change in potential of the probe tip is detected, the controller using the position of the probe as a first end point of the second axis,
   direct the motors to move the probe in the reverse direction over the second axis until a second change in potential of the probe tip is detected, the controller using the position of the probe as a second end point of the second axis, and
   calculate a two-dimensional center of the given target well as the mid-point between the two ends points of the second axis.

3. The system of claim 2 wherein the controller further verifies the location of the center by moving the probe from the center location along the first axis until the change in potential is detected and checking if the probe has moved a distance that corresponds to the calculated mid-point of the first axis.

4. The system of claim 1 wherein the motors are stepper motors that move along associated slides in axial directions.

5. The system of claim 4 further including
   a plurality of sensors, each of which is placed to detect the position of a given one of the stepper motors proximate to an end of an associated slide, and
   the controller further configured to:
      direct the stepper motors to move in axial directions until the sensors detect the positions of the stepper motors at the ends of the slides to determine maximum positions along the slides,
      calculate zero positions along each axis by subtracting predetermined maximum lengths from the maximum points, and
      set a home position of the probe as the coincidence of the zero positions of the axes, and
      determine the distance of the centers of the target wells relative to the home position.

6. The system of claim 1 further comprising:
   additional wells that are spaced by predetermined distances from the target wells, and
   the controller further configured to direct the motors to move the probe to a given additional well based on the calculated center locations of one or more target wells and the predetermined distances.

7. The system of claim 6 wherein
   the additional wells and the target wells are arranged in a grid, and
   the controller determines skew across rows and columns of the grid based on differences in axial coordinates of the centers of the target wells.

8. The system of claim 1 wherein the dimensions are along linear axes, angular axes or a combination of linear and angular axes.

9. An automated alignment system for a differential scanning calorimetry system consisting of:
   a plurality of wells held at a first potential;
   a probe having a tip held at a second potential;
   one or more motors for moving the probe relative to the wells; and
   a controller configured to:
      detect changes in potential at the probe,
      direct the motors to move the probe to an estimated position in which the probe tip extends within a given well and move the probe along first and second axes to determine dimensions of the given well by determining first and second end points of the first and second axes as the locations at which the potential at the probe tip changes along the first and second axes,
      direct the motors to move the probe along a third axis into electrical contact with a floor of the given well based on a change in potential at the probe tip, and
      calculate a center location of the given well as the coincidence of mid-points of the first, second and third axes that are calculated based on the endpoints of the first and second axes, and a mid-point of the third axis calculated based on a location of the floor of the given well and a known depth of the given well.

10. The system of claim 9 wherein
    the wells are furnace wells that are within furnaces and sample wells that are arranged in a sample tray that is held at a low DC potential, and the controller further configured to:
       direct the motors to move the probe to a position above a flat section of a top surface of the sample tray adjacent to a given sample well and lower the probe to contact the top surface,
    determine a relative height of the top surface based on the position of the probe at contact and determines a minimum position for lowering the probe into the given sample well during alignment as a predetermined distance below the relative height.

11. The system of claim 10 further including
    lid wells in the sample tray, and
    the controller further configured to determines a minimum distance to lower the probe into a given lid well during alignment based on a relative height determined at a flat surface adjacent to the given lid well.

12. The system of claim 11 wherein the controller is further configured to:
    direct the motors to move the probe into an estimated position above a given furnace well and lower the probe down into the furnace well along the third axis until the change in potential at the probe is detected to indicate the floor of the well,
    determine a center position along the third axis based on the position of the probe, and
    calculate the center location of the furnace well at the mid-points of the first and second axes and the center of the third axis.

13. The system 12 wherein the controller further configured to:
    direct the motors to move the probe into one or more selected sample wells and move the probe within the respective sample wells along x and y axial dimensions until changes in the potential at the probe are detected to indicate the first and second axes of the sample wells, calculate center locations of the respective sample wells at the mid-points of the first and second axes, and use the calculated center locations of the sample wells and the furnaces to direct the motors to move the probe between the center of a given sample well to the center of a given furnace.

14. The system of claim 13 wherein the controller uses the calculated center locations of the lid wells to direct the probe between the lid wells and the furnaces.

15. The system of claim 14 wherein
the probe includes a vacuum outlet,
the sample wells contain sample pans,
the lid wells contain lids, and
the controller further configured to:
 direct the motors to move the probe to the calculated center location of a given sample well and lower the probe a predetermined distance into the well,
 control a vacuum that provides suction through the vacuum outlet to pick up and carry the sample pan contained in the given sample well,
 direct the motors to move the probe carrying the sample pan to the calculated center location of a selected furnace well,
 control the vacuum to release the sample pan, and
 move the probe out of the furnace that includes the selected furnace well.

16. The system of claim 15 wherein the controller configured to:
 direct the motors and vacuum to move the probe to a given lid well to pick up a lid contained therein, transport the lid to the furnace that includes the selected furnace well, and
 release the lid to cover the sample pan contained therein.

17. The system of claim 16 wherein the controller further configured to:
 direct the motors to move the probe to the center of the selected furnace well and controls the vacuum to provide suction to pick up the lid,
 direct the motors to move the probe to the center of the given lid well and controls the vacuum to release the lid,
 direct the motors to move the probe to the furnace that includes the selected furnace well and controls the vacuum to provide suction to pick up the sample pan, directs the motors to move the probe to the center of the given sample well and controls the vacuum to release the sample pan.

18. The system of claim 16 wherein the controller is further configured to determines that the probe has encountered an obstacle if back-pressure at the vacuum outlet indicates that the probe has picked up something before the probe has moved to a position in which the probe is expected to pick up one of the sample pan and the lid.

19. The system of claim 18 wherein the controller is further configured to determine that the probe has dropped the sample pan or the lid if the back-pressure at the vacuum outlet decreases before the vacuum is controlled to release the sample pan or the lid.

20. A method of aligning a probe to wells comprising:
 holding the probe at one potential and holding the wells at a different potential;
 moving the probe to an estimated center position above a selected well;
 lowering the probe into the selected well;
 moving the probe in positive and negative directions along first and second axial dimensions until changes in potential are detected at the probe to indicate electrical contact between the probe and end points along the first and second axial dimensions of the selected well;
 moving the probe along a third axial dimension into electrical contact with a floor of the selected well based on a change in potential at the probe; and
 calculating center location of the selected well as the coincidence of mid-points of the first, second and third axial dimensions that are calculated based on end points of the first and second axial dimensions, and a mid-point of the third axial dimension based on a location of the floor of the selected well and a known depth of the selected well.

21. The method of claim 20 further including determining center locations for other wells based on known spacing between wells and the calculated center locations of the selected well.

* * * * *

UNITED STATES PATENT AND TRADEMARK OFFICE
CERTIFICATE OF CORRECTION

PATENT NO. : 8,296,962 B2
APPLICATION NO. : 12/730797
DATED : October 30, 2012
INVENTOR(S) : Keith S. Ferrara et al.

It is certified that error appears in the above-identified patent and that said Letters Patent is hereby corrected as shown below:

In the Claims:

In col. 12, line 45 should read:
The controller further configured to determine~~s~~ a minimum In col. 14, line 8 should read:
Configured to ~~determines~~ determined that the probe has encountered an Signed and Sealed this
Eleventh Day of June, 2013

Teresa Stanek Rea
*Acting Director of the United States Patent and Trademark Office*